United States Patent [19]
Shipcott

[11] Patent Number: 5,245,709
[45] Date of Patent: Sep. 21, 1993

[54] PROTECTIVE EYEWARE

[76] Inventor: Kurtis R. Shipcott, 13552 Whembly Dr., Santa Ana, Calif. 92705

[21] Appl. No.: 944,647

[22] Filed: Sep. 14, 1992

[51] Int. Cl.⁵ ............................................. A61F 9/04
[52] U.S. Cl. ................................................. 2/425; 2/9; 2/426; 2/428; 2/430; 2/436; 2/449
[58] Field of Search .................... 2/101, 171, 304, 308, 2/312, 425, 426, 428, 430, 431, 432, 435, 436, 437, 439, 445, 447, 448, 449, 452, 454, 9, 15, 12

[56] References Cited
U.S. PATENT DOCUMENTS

| | | | |
|---|---|---|---|
| 540,746 | 6/1895 | Lamb | 2/439 |
| 1,584,476 | 5/1926 | Schalow | 2/308 |
| 2,296,634 | 9/1942 | Fink | 2/447 |
| 3,671,976 | 6/1972 | Johnson et al. | 2/430 |
| 4,610,036 | 9/1986 | La Prairie | 2/450 X |
| 4,797,956 | 1/1989 | Boyce | 2/431 |
| 4,850,058 | 7/1989 | Cheng | 2/439 |
| 5,016,292 | 5/1991 | Rademacher | 2/431 |
| 5,138,714 | 8/1992 | Smith | 2/439 X |

OTHER PUBLICATIONS

Unnumbered page (p. 125?) of Jan. 1988, Surfer magazine, vol. 29, No. 1.
2 page advertisement dated Jul. 1992, from Specusa-for amphibius eye ware, Sports Eyes Ent., Inc., P.O. Box 2537, Costa Mesa, Calif. 92628.

*Primary Examiner*—Clifford D. Crowder
*Assistant Examiner*—Jeanette E. Chapman
*Attorney, Agent, or Firm*—James G. O'Neill

[57] ABSTRACT

Protective eyeware for a board user includes a substantially thin, one-piece body made from a clear, flexible material having color and ultraviolet protection added thereto. The body includes wing shaped edges which fit over the temples of a wearer and have an elastic headband secured to their ends for retaining the eyeware on the head of a wearer. A plurality of resilient members are secured to the interior of the body so as to fit against the face of a user in the wearing position and to provide a plurality of spaces for the passage of air and water between the interior surface of the body and the face of the user. The headband is provided with a leash means having a strap secured thereto, for fixing of the eyeware to the neck of the wearer by means of a collar connected to the strap, or by means of the strap being directly connected to a garment worn by the user.

16 Claims, 2 Drawing Sheets

PROTECTIVE EYEWARE

BACKGROUND OF THE INVENTION

1. Field of the Invention

This invention relates generally to protective eyeware and, more particularly, to protective eyeware to be worn while engaged in water sports.

2. Description of Related Art

Water sports using various type boards, such as boogie boarding, surfing, and the like, have become increasingly popular over the last few decades. Such water oriented activities now represent major recreational sports in fresh water, man-made facilities, and particularly in the oceans of the world. With the tremendous rise in persons participating in these sports, the need has increased to protect the participants, eyes from the harmful rays of the sun as well as from water spray, such as caused by wind or the action of waves. However, no generally acceptable eyeware has been available or adopted by surf board riders or other participants in related water oriented sports.

As is well known, the eyes of a person must be protected from the harmful rays of the sun, since prolonged exposure can cause serious eye damage. Furthermore, in connection with surfing and related water oriented sports, there is an even greater need for protection from ultraviolet rays entering the surfer's eyes, directly from the sun, and reflected off of the water and other surfaces.

Harmful solar rays, such as ultraviolet rays, exist on both sunny and overcast days, with the harmful effect being further intensified on bright sunny days, because of the reflection of the light from the surface of the water. Furthermore, particularly on sunny days, when ocean surfers sit on their surfboards, between wave sets, the glare of reflected light causes significant discomfort and irritation. This reflected light can become dangerous, if the surfer's vision is impaired so as to prevent the surfer from seeing oncoming waves and/or other objects, persons or surfers.

There is a further need for protective eyeware to protect a surfer's eyes form the impairment in or total loss of vision caused by ocean spray or other water resulting from high winds or ocean wave action. For example, when a surfer makes the initial drop down a wave, or rides into the wind, a spray of water is often scooped off the surface of the water and carried with the wind, hitting the surfer in the eyes, causing impairment in or temporary loss of vision until the surfer's eyes are cleared. Because the surfer is moving fast and powerfully at such times, this temporary impairment in or loss of vision may result in a collision with another surfer, swimmer or object, potentially causing severe injury or worse, to the surfer(s) and/or another person.

Available sunglasses are not practical for use by a surfer, as they fall off easily, do not adequately protect the eyes from peripheral spray and ultraviolet light, and are easily knocked off or lost when surfer moves his head too fast, or impacts the water at any number of angles, especially when the surfer is pummeled by powerful wave action. Additionally, when a fallen surfer emerges from under water, there is a very strong natural desire to want to clear the eye pockets of collected water, by rubbing the eyes with the fingers, in a clearing motion. Thus, even in the mildest surf, known glasses are impractical, even if still held on the surfer's head by some means, since the natural tendency to clear the eyes by the fingers would unsettle the glasses from the surfer's face.

Other known devices, such as motorcycle, skiing and swimming type goggles, usually include surrounding frames or supports, which cut-off or retard peripheral vision. Or, such goggles can easily fill with moisture or water, and must be lifted from the face to clear out the moisture or water. These goggles are also subject to the formation of condensation and/or fog on interior of their lenses, and must be removed so as to clear the lens interiors of any such condensation or fog. Also, such goggles would be easily knocked off and lost in the surf when dislodged from the face of a surfer.

When a surfboard rider is moving on the water, the surfer's hands and arms should be free for paddling, to enable the rider to catch a wave, or provide balance while standing on the board. Therefore, during such times, it is not practical for a surfer to adjust any protective eyeware, and any of these available sunglasses or goggles are not acceptable for use by a surfer.

Further prior art goggles proposed for use as surf eyeware include a pair of no--flexible lenses attached outwardly on mounts carried on a frame that completely surrounds the eyes. However, the frame of these goggles prevents easy access for finger tip clearing of the eye pockets, and has, among other drawbacks, undesirable bulk.

Also known in the prior art are eyeglasses having a non-flexible pair of glass lenses in a surrounding rigid, eyeglass frame with a string like cord tied to a headband and a collar. Neither the surf goggles mentioned in the paragraph directly above nor the eyeglasses and string cord holding means mentioned in this paragraph meet all the needs of a board rider or overcome the deficiencies mentioned herein.

in view of the above, it can be readily seen that there is a substantial need for protective eyeware to be worn by a surfer or the like, to retard the harmful effects of ultraviolet rays when on the water. There also exists the need for such eyeware to protect a surfer's eyes from impairment in or temporary loss of vision resulting from the spray of water caused by waves and wind. Additionally, there exists a need for such eyeware which retards fog and/or condensation buildup therein, and which is easily removed form the interior of the lens of the eyeware, without the need to remove the eyeware. And, more importantly, there exists the need for such eyeware that may be fastened securely so as not to be easily dislodged, nor easily lost in surf, or during vigorous board activity.

The present invention meets all of the above described needs by the provision of protective eyeware that may be worn by a surfer or other board user in the water. This eyeware is worn by the surfer in such a manner that it remains securely held in place to provide the desired protection from ultraviolet rays and the spray of water, but allows ready access to the eyes for removal of water therefrom.

SUMMARY OF THE INVENTION

It is, therefore, a general object of the present invention to provide protective eyeware for use in the water. It is a more particular object of the present invention to provide protective eyeware that may be worn by a surfer. It is a further object of the present invention to provide protective eyeware for use by a surfer, in the water, and which provide protection from both the ultraviolet rays of the sun and blinding water spray, as well as shade for the eyes of the user. It is yet another object of the present invention to provide protective eyeware for a surfer which provides the user with unobstructed peripheral vision. It is a still further object of the present invention to provide protective eyeware for a surfer wherein the buildup of condensation or fogging on the interior of the lens is retarded, and may be easily removed without the need to remove the eyeware. It is yet a still further object of the present invention to provide protective eyeware for a surfer that allows for easily clearing water from the eye pockets of the user, without the need to remove the eyeware. And it is still another object of the present invention to provide protective eyeware that is securely held on the user and which includes leash means to prevent its loss in ocean surf, in case of accidental loosening thereof.

In accordance with the present invention there is provided protective eyeware for wearing by a surfer having a one-piece body made from a clear, thin, flexible material with color and ultraviolet protection added thereto. The body includes wing shaped ends which flexibly fit over the eyes and wrap around the temples of a wearer. The eyeware is secured to the wearer by an elastic headband attached to the wing shaped ends and cooperates with the flexible body to retain the eyeware in position wrapped around the eyes and temple areas of the wearer. A plurality of resilient members are secured to the interior of the body and fit against the face of the wearer to secure the body against the face of the wearer, while providing a plurality of spaces for the passage of air and water between the interior surface of the body and the face of the wearer. Additionally, these resilient members provide sufficient buoyancy to the eyeware to float the same if dropped into water. The headband is provided with a leash means having a strap secured thereto, for fixing of the eyeware to the wearer to prevent loss thereof.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for a novel combination protective eyeware and securing means, for wearing by a board user in water, such as by a surfer in the ocean.

Figure 1:
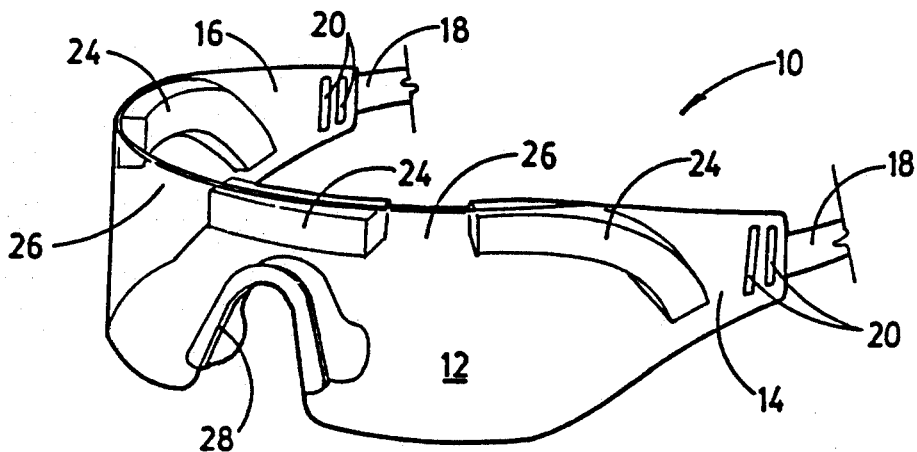
FIG. 1 is a perspective view of an embodiment of the protective eyeware of the present invention having a curved body.
Figure 4:
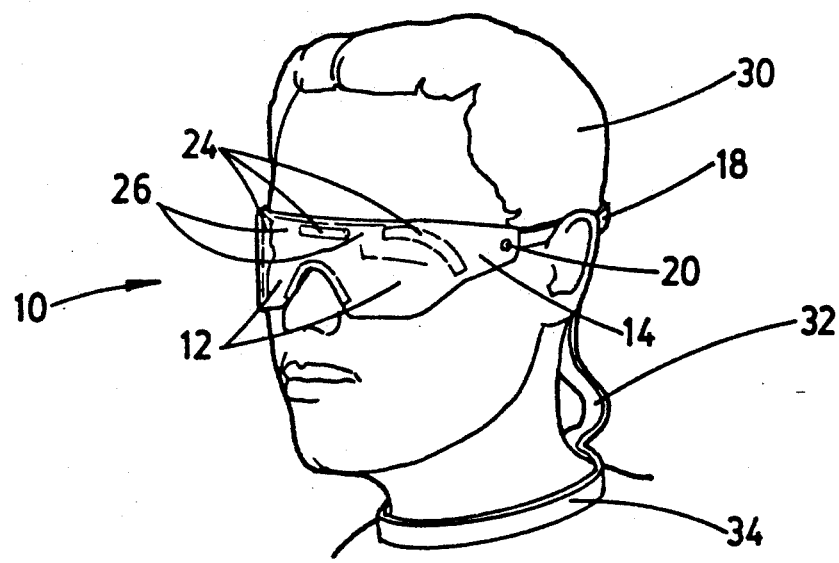
FIG. 4 is a perspective view of the head of a person wearing a pair the protective eyeware of FIG. 1, together with a preferred embodiment of the leash securing means to prevent the loss of the eyeware.

As shown in FIGS. 1 and 4, protective eyeware 10 is preferably designed with a curved body or lens 12, so as to shade the eyes of a wearer 30, as well as provide ultraviolet protection and protection from water spray. The curved body or lens 12, is preferably constructed, in any known manner, such as by molding, from a single piece of substantially thin, clear, flexible material. The body 12 does not have a frame or support, and includes a centrally removed area for the nose of a wearer, and is of sufficient flexibility to enable it to be flexed or forced into a shape that enables it to be wrapped around a wearer's eyes and extend to a wearer's temples so as to completely shade the eyes of a wearer. Any known flexible material that is clear, thin and light in weight and provides the necessary flexibility, shading, ultraviolet and water spray protection, such as a mono layer of butyrate, cellulosic acetate, a light polarizing plastic, or the like, may be used to form the lens. The body or lens 12 may contain the ultraviolet protection, preferably an ultraviolet inhibitor, added or applied thereto in a manner known to those skilled in the art. Furthermore, the lens, although clear, is preferably colored, shaded or tinted, in a manner known to those skilled in the art, to enable the user to see, but to provide the necessary glare protection to the user's eyes while on the water. The material may be made in any desired color or tint; for example, smoke, to shade the eyes of a wearer and/or retard the effect of glare on bright days; or amber, to enhance contrast for overcast days.

Figure 2:
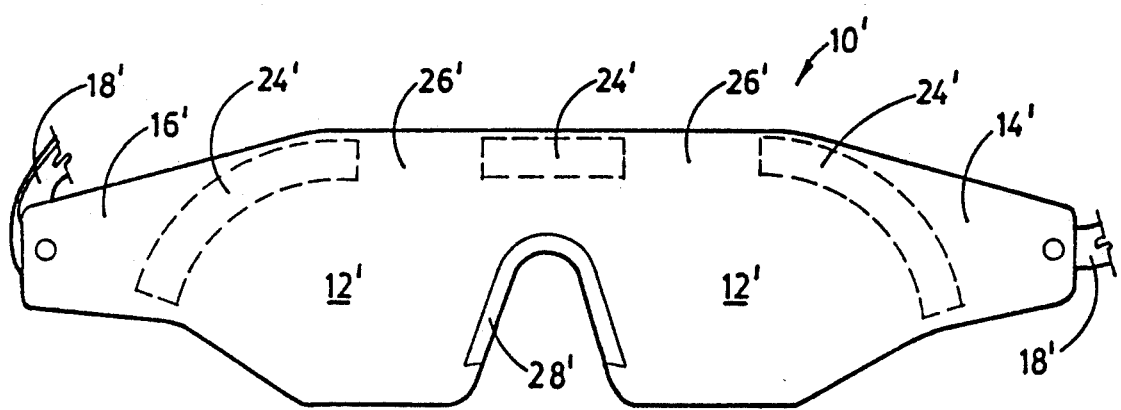
FIG. 2 is a front elevational view of an embodiment of the protective eyeware of the present invention having a flattened body.
Figure 3:
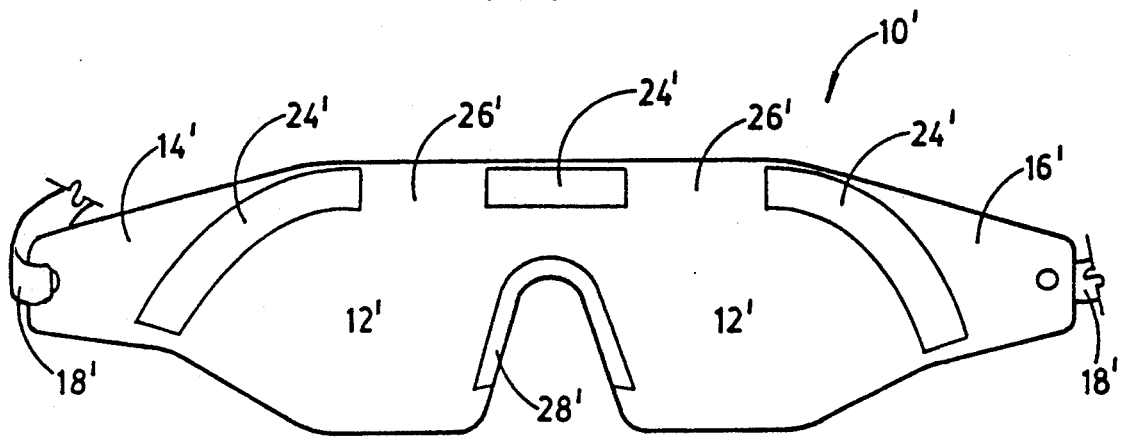
FIG. 3 is a rear elevational view of the protective eyeware of FIG. 2.
Figure 6:
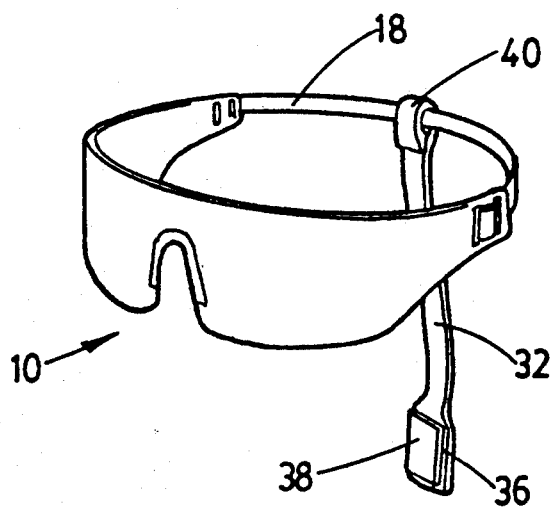
FIG. 6 is a perspective view of the protective eyeware of FIG. 1, together with another embodiment of the leash securing means to prevent the loss of the eyeware.

The body or lens 12 is preferably provided with a preset curved shape, as shown in FIGS. 1, 4 and 6, without the need of a frame or support. Furthermore, if desired, the protective eyeware may be formed with a flat body 12' having no frame or support, as indicated at 10' in FIGS. 2 and 3. In either version, the body or lens 12, 12', is preferably a clear, flexible, single piece of lightweight material that includes a lens portion with the centrally located nose area and elongated, tapering, wing shaped ends or temple portions 14, 14' and 16, 16' which may be seen through and are of sufficient length to be wrapped around the eyes and contact both temple areas of a wearer's head, when secured thereon by a head band 18, 18'. The headband 18, 18' for either version is preferably formed from an elastic material, such as one or more elongated rubber bands of any desired width and strength, and may be made in a variety of colors. The headband 18, 18' is secured to outer tips of the wing shaped ends 14, 14' and 6, 16', in any known manner, as by being threaded through a plurality of openings 20 formed adjacent the tip ends, so as to be adjustable, or fixed thereto by pin or rivet type means. It, therefore, can be seen that the headband allows for a proper and firm fit of the eyeware to the face of a wearer from around the eyes to the temples. The flexible, lightweight material forming the body 12, 12' of the eyeware 10, 10', together with the elasticity of the headband, allows the eyeware 10, 10' to be bent/shaped to a secure and custom, wrapped-around or curvature fit to a wearer's head, as shown more clearly in FIG. 4 (for eyeware 10).

To ensure that the tight fit for the eyeware 10, 10' is comfortable on a wearer's face, the body 12, 12' includes a plurality of elongated, soft or yielding members 24, 24' fixed thereto on the interior surface thereof, to contact the face of the wearer. For example, by way of explanation only, and not by way of limitation, the body 12, 12' is shown as having three members 24, 24', two of which are curved, for contacting the area of a wearer's face, approximately around the eyes, toward the temples, and the other of which is substantially straight, and placed so as to contact the face of the wearer, approximately between the eyes on the wearer's forehead (see FIG. 4). The elongated members 24, 24' are fixed to the interior surface of the body 12, 12' in any known manner, as by gluing. These members 24, 24' are preferably formed from a waterproof material, such as a closed cell sponge or rubber tubing that will not absorb water. The elongated members must be of sufficient thickness to keep the eyeware raised, or away from the wearer's face, and may be of any desired color, or a variety of colors. Furthermore, the members 24, 24' must be of sufficient size and mass to provide for both a comfortable, tight facial fit, and so as to provide sufficient buoyancy to cause the lightweight eyeware 10, 10' (including any headband and securing means) to float in water, if the eyeware is somehow dislodged from a wearer's head, or dropped by a user.

As shown, a plurality of spaces 26, 26' are provided between the plurality of elongated members 24, 24' to enable air and water to flow freely through these spaces. It is to be understood that if additional elongated members are added to the interior surface of the body, or the elongated members shown are cut or made smaller, that additional spaces would be formed therebetween to allow for additional flow of air and water therebetween. As described above, the members 24, 24' must be of sufficient thickness to hold the body or lens 12, 12' away from or out from the face of a wearer so as to allow for space between the interior surface of the body and the face of the wearer, in particular, around the facial cheek areas. This space between the face of the wearer and the interior surface of the body 12, 12' of the eyeware 10, 10', enables the free flow of air and water past the eyes and covered face areas. Furthermore, this space allows a wearer's finger tips to be inserted under the lens to easily wipe the covered eye pockets so as to remove any water therein, without requiring removal of the eyeware. This wiping of the eye pockets by the wearer's finger tips, with the eyeware in place, is made possible by the flexibility of the lens 12, 12' and the elasticity of headband 18, 18', holding the eyeware in position, since they allow sufficient flexing and/or outward movement of the body or lens.

A nosepiece 28, 28', preferably formed with a grove therein, is secured to the narrowed or shaped, centrally located nose area of the one piece body or lens 12, 12'. Nosepiece 28, 28' is preferably constructed from a waterproof material, such as rubber or the like, and fixed or secured in place in lens 12, 12', as by gluing. The nosepiece must be sufficiently thick to hold the lens 12, 12' away from the nose and surrounding areas of the face of the wearer to assist in allowing the wearer to wipe clear the eye pockets and provide free air and water flow spaces, as described above. The nosepiece 28, 28' may be made from a clear material, or may also be of any desired color.

As shown more clearly in FIGS. 4-7, the elastic headband 18, 18, of the eyeware 10, 10' is preferably connected to or formed integrally with a leash means 32. The elastic headband and leash means allows the eyeware to be used actively, since the leash acts as a safety or security device to hold onto the eyeware so that the wearer may easily retrieve and, therefore, not loose the eyeware, if somehow dislodged, when wearing. The leash means 32 may be composed solely of an elongated strap 32, or may include the elongated strap 32 and a collar 34 fastened to a first end 36 of the strap. Preferably, both the collar 34 and the strap 32 are made from an elastic material. First end 36 of strap 32 may be permanently fixed to the collar, in any known manner, or may be releasably connected thereto, by any known means, such as a Velcro fastening means 38. A second end 40 of the strap 32 is permanently secured to the headband 18, as by being glued or sewn thereto, or releasably held therearound, as by means of a Velcro fastening means 42.

Figure 5:
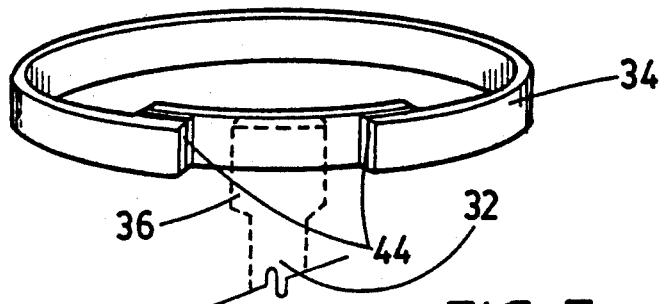
FIG. 5 is a perspective view of the leash securing means of FIG. 4.

As shown in FIGS. 4 and 5, when the leash means includes the collar 34, the second end 40 of elongated strap 32 is fastened to or around the headband 18 and the first end 36 is fastened to the collar 34. The collar 34 is then secured around the neck of the wearer 30, as shown in FIG. 4. The collar 34 may be elastic and of a single piece construction, or may be made from one or more elastic or non-elastic pieces of material having one or more adjustable securing means 44, such as Velcro-type closure means, so as to be easily opened and adjustably secured around the neck of the wearer 30.

Figure 7:
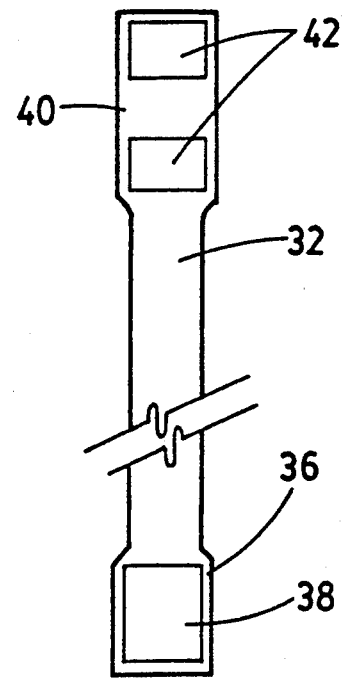
FIG. 7 is a front elevational view of the securing means of FIG. 6.

As shown more clearly in FIGS. 6 and 7, when the strap 32 is used alone as a leash means, its second end 40 is secured to or fastened around the headband 18, and its first end 36 has the velcro fastening means 38 fixed to a complementary fastener, such as a Velcro patch (not shown), fixed to the top or collar portion of a wet suit or other garment worn by the wearer 30. The components of the leash, may be made of any desirable material, in any available color.

It, therefore, can be seen that the present invention provides novel protective eyeware having a flexible lens which shades the eyes of a wearer, provides protection from ultraviolet rays, does not block peripheral vision, and provides protection from water spray. The eyeware is constructed so as to be sufficiently flexible to wrap around the eyes of a wearer so as to extend to the temple areas of the wearer's face, and provide a custom fit. The eyeware, therefore, will also block the blinding effect of direct head-on and side water spray, while allowing desirable air and water flow channels and spaces between the interior surface of the lens and the face and eyes of the wearer. Additionally, the elastic headband securing the protective eyeware to the head of a user is preferably combined with a leash means to retain dislodged eyeware adjacent the wearer, for prevention of loss and easy retrieval.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. Protective eyeware to be worn on a wearer's head, over a wearer's face in the water, to protect a wearer's eyes from both harmful solar rays and water spray, including, in combination:

a clear, one-piece substantially thin, flexible body forming a flexible lens to shade said wearer's eyes, without blocking peripheral vision of said wearer's eyes, and further providing ultraviolet protection while substantially blocking water spray from hitting said wearer's eyes;

said clear, one-piece, substantially thin, flexible body having interior and exterior surfaces with a lens portion, a centrally located nose area having a nosepiece secured therein, and a pair of clear, substantially thin, flexible, elongated, tapering, temple portions extending outwardly from said lens portion;

said pair of clear, substantially thin, flexible, elongated, tapering, temple portions ending in substantially narrow tip ends;

a plurality of elongated flexible members secured to the interior surface of said clear, one-piece substantially thin, flexible body for placement against portions of said wearer's face;

a plurality of spaces formed between said elongated flexible members to allow the flow of air and water between said interior surface of said body and the face of said wearer, when said protective eyeware is secured in position on said wearer's head covering said wearer's eyes; and an elastic headband secured to said substantially narrow tip ends for securing said protective eyeware to said wearer's head, with said clear, one-piece, substantially thin, flexible body wrapped around said wearer's eyes and said substantially narrow tip ends extending to and held against the temple areas of said wearer's face.

2. The protective eyeware of claim 1 wherein said elongated flexible members secured to the interior surface of said clear, one-piece, substantially thin, flexible body have sufficient mass and buoyancy to float said protective eyeware in water.

3. The protective eyeware of claim 2 wherein there are at least three elongated flexible members secured to there interior surface of said clear, one-piece, substantially thin, flexible body.

4. The protective eyeware of claim 2 wherein said elastic headband is adjustably secured in a plurality of openings formed in said substantially narrow tip ends.

5. The protective eyeware of claim 4 wherein said clear, one-piece, substantially thin, flexible body forming a flexible lens is formed from a preset curved piece of flexible material.

6. The protective eyeware of claim 5 wherein said clear, one-piece, substantially thin, flexible body forming a flexible lens is in any desired color and tint.

7. The protective eyeware of claim 4 wherein said clear, one-piece, substantially thin, flexible body forming a flexible lens is formed from a flat piece of flexible material.

8. The protective eyeware of claim 7 wherein said clear, one-piece, substantially thin, flexible body forming a flexible lens is in any desired color and tint.

9. The protective eyeware of claim 7 wherein said clear, one-piece, substantially thin, flexible body forming a flexible lens is in any desired color and tint, to enhance contrast for overcast days.

10. The protective eyeware of claim 1, further including a leash means, attached to said elastic headband to prevent the loss of said protective eyeware.

11. The protective eyeware of claim 10 wherein said leash means comprises a strap having two ends, one of the ends of the strap adapted to be attached to said elastic headband, and the other of the ends of the strap adapted to be attached to a garment worn by said wearer.

12. The protective eyeware of claim 11 wherein said two ends of said strap have releasable holding means thereon, so as to be releasably attached to said elastic headband and said garment worn by said wearer.

13. The protective eyeware of claim 12 wherein said elongated flexible members secured to the interior surface of said clear, one-piece, substantially thin, flexible body have sufficient mass and buoyancy to float said protective eyeware and said strap in water.

14. The protective eyeware of claim 10 wherein said leash means comprises a strap having two ends and a collar, one of the ends of the strap adapted to be attached to said elastic headband, and the other of the ends of the strap adapted to be attached to said collar, which collar may be worn around a neck of a wearer.

15. The protective eyeware of claim 14 wherein said two ends of said strap have releasable holding means thereon, so as to be releasably attached to said elastic headband and said collar, and said collar includes releasable and adjustable holding means so as to be capable of being adjustably worn around said neck of said wearer.

16. The protective eyeware of claim 15 wherein there are at least three elongated flexible members secured to the interior surface of said clear, one-piece, substantially thin, flexible body and these flexible members have sufficient mass and buoyancy to float said protective eyeware, said strap and said collar in water.

* * * * *